(12) United States Patent
Yaniv et al.

(10) Patent No.: US 11,944,444 B2
(45) Date of Patent: Apr. 2, 2024

(54) PREDICTING VENTRICULAR FIBRILLATION

(71) Applicant: TECHNION RESEARCH & DEVELOPMENT FOUNDATION LIMITED, Haifa (IL)

(72) Inventors: Yael Yaniv, Haifa (IL); Noam Keidar, Haifa (IL); Gal Eidelsztein, Haifa (IL); Alex Bronstein, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 559 days.

(21) Appl. No.: 17/274,293

(22) PCT Filed: Sep. 5, 2019

(86) PCT No.: PCT/IL2019/050999
§ 371 (c)(1),
(2) Date: Mar. 8, 2021

(87) PCT Pub. No.: WO2020/049571
PCT Pub. Date: Mar. 12, 2020

(65) Prior Publication Data
US 2021/0330238 A1 Oct. 28, 2021

Related U.S. Application Data

(60) Provisional application No. 62/727,611, filed on Sep. 6, 2018.

(51) Int. Cl.
*A61B 5/361* (2021.01)
*A61B 5/00* (2006.01)
(Continued)

(52) U.S. Cl.
CPC .......... *A61B 5/361* (2021.01); *A61B 5/02405* (2013.01); *A61B 5/02416* (2013.01);
(Continued)

(58) Field of Classification Search
CPC . A61B 5/361; A61B 5/02405; A61B 5/02416; A61B 5/0245; A61B 5/7267; A61B 5/74; G16H 50/20; G06N 20/00
See application file for complete search history.

(56) References Cited

U.S. PATENT DOCUMENTS 4,750,494 A 6/1988 King
7,162,299 B1 1/2007 Kroll et al.
(Continued)

FOREIGN PATENT DOCUMENTS

| CN | 102058407 A | 5/2011 |
| CN | 106562777 A | 4/2017 |
| RU | 1806380 C | 3/1993 |

OTHER PUBLICATIONS

Li X, Dong Z. Detection and prediction of the onset of human ventricular fibrillation: an approach based on complex network theory. Phys Rev E Stat Nonlin Soft Matter Phys. Dec. 2011;84(6 Pt 1):062901. doi: 10.1103/PhysRevE.84.062901. Epub Dec. 12, 2011. PMID: 22304137.
(Continued)

*Primary Examiner* — Catherine M Voorhees
*Assistant Examiner* — Roland Dinga
(74) *Attorney, Agent, or Firm* — The Roy Gross Law Firm, LLC; Roy Gross (57) ABSTRACT

A method comprising: at a training stage, training a machine learning algorithm on a training set comprising: (i) Heart Rate Variability (HRV) parameters extracted from temporal beat activity samples, wherein at least some of said samples include a representation of a Ventricular Fibrillation (VF)
(Continued)

event, (ii) labels associated with one of: a first period of time immediately preceding a VF event in a temporal beat activity sample, a second period of time immediately preceding the first period of time in a temporal beat activity sample, and all other periods of time in a temporal beat activity sample; at an inference stage, receiving, as input, a target HRV parameters representing temporal beat activity in a subject; and applying said machine learning algorithm to said target HRV parameters, to predict an onset time of a VF event in said subject.

19 Claims, 3 Drawing Sheets

(51) Int. Cl.
| | |
|---|---|
| *A61B 5/024* | (2006.01) |
| *A61B 5/0245* | (2006.01) |
| *G06N 20/00* | (2019.01) |
| *G16H 10/60* | (2018.01) |
| *G16H 50/20* | (2018.01) |

(52) U.S. Cl.
CPC .......... *A61B 5/0245* (2013.01); *A61B 5/7267* (2013.01); *A61B 5/74* (2013.01); *G06N 20/00* (2019.01); *G16H 10/60* (2018.01); *G16H 50/20* (2018.01)

(56) References Cited

U.S. PATENT DOCUMENTS

| | | | |
|---|---|---|---|
| 7,218,960 | B1 | 5/2007 | Min et al. |
| 2003/0191403 | A1 | 10/2003 | Zhou et al. |
| 2007/0038254 | A1 | 2/2007 | Thong |
| 2010/0030293 | A1 | 2/2010 | Sarkar et al. |
| 2013/0006317 | A1 | 1/2013 | Keel et al. |
| 2015/0265174 | A1 | 9/2015 | Shakibi Gilani |
| 2016/0135706 | A1* | 5/2016 | Sullivan .................. A61B 7/003 600/509 |
| 2018/0146929 | A1* | 5/2018 | Joo ....................... A61B 5/0816 |
| 2018/0242863 | A1* | 8/2018 | Lui ....................... A61B 5/7275 |
| 2021/0282692 | A1 | 9/2021 | Yaniv et al. |

OTHER PUBLICATIONS

Nearing BD, Verrier RL. Modified moving average analysis of T-wave alternans to predict ventricular fibrillation with high accuracy. J Appl Physiol (1985). Feb. 2002;92(2):541-9. doi: 10.1152/japplphysiol.00592.2001. PMID: 11796662.
Sarusi A, Rárosi F, Szücs M, Csik N, Farkas AS, Papp JG, Varró A, Forster T, Curtis MJ, Farkas A. Absolute beat-to-beat variability and instability parameters of ECG intervals: biomarkers for predicting ischaemia-induced ventricular fibrillation. Br J Pharmacol. Apr. 2014;171(7):1772-82. doi: 10.1111/bph.12579. PMID: 24417376; PMCID: PMC3966755.
Goldberger AL, Amaral LA, Glass L, Hausdorff JM, Ivanov PC, Mark RG, Mietus JE, Moody GB, Peng CK, Stanley HE. PhysioBank, PhysioToolkit, and PhysioNet: components of a new research resource for complex physiologic signals. Circulation. Jun. 13, 2000;101(23):E215-20. doi: 10.1161/01.cir.101.23.e215. PMID: 10851218.
Sedehi, Javid Farhadi & Jafarnia Dabanloo, Nader & Attarodi, Gholamreza & Zadeh, Mehdi. (2017). The Prediction of Ventricular Fibrillation based upon HRV Signal Using Combination of Genetic Algorithm and Neural Networks. 10.22489/CinC.2017.103-255.
Kim H, Ishag MIM, Piao M, Kwon T, Ryu KH. A Data Mining Approach for Cardiovascular Disease Diagnosis Using Heart Rate Variability and Images of Carotid Arteries. Symmetry. 2016; 8(6):47. https://doi.org/10.3390/sym8060047.
Rajpurkar, P., Hannun, A. Y., Haghpanahi, M., Bourn, C., & Ng, A. Y. (2017). Cardiologist-level arrhythmia detection with convolutional neural networks. arXiv preprint arXiv:1707.01836.
Tang PT, Shenasa M, Boyle NG. Ventricular Arrhythmias and Sudden Cardiac Death. Card Electrophysiol Clin. Dec. 2017;9(4):693-708. doi: 10.1016/j.ccep.2017.08.004. PMID: 29173411.
Dresen WF, Ferguson JD. Ventricular Arrhythmias. Cardiol Clin. Feb. 2018;36(1):129-139. doi: 10.1016/j.ccl.2017.08.007. Epub Oct. 27, 2017. PMID: 29173673.
Nichol G, Sayre MR, Guerra F, Poole J. Defibrillation for Ventricular Fibrillation: A Shocking Update. J Am Coll Cardiol. Sep. 19, 2017;70(12):1496-1509. doi: 10.1016/j.jacc.2017.07.778. PMID: 28911514.
Gianotto-Oliveira R, Gonzalez MM, Vianna CB, Monteiro Alves M, Timerman S, Kalil Filho R, Kern KB. Survival After Ventricular Fibrillation Cardiac Arrest in the Sao Paulo Metropolitan Subway System: First Successful Targeted Automated External Defibrillator (AED) Program in Latin America. J Am Heart Assoc. Oct. 9, 2015;4(10):e002185. doi: 10.1161/JAHA.115.002185. PMID: 26452987; PMCID: PMC4845117.
Cheskes S, Schmicker RH, Christenson J, Salcido DD, Rea T, Powell J, Edelson DP, Sell R, May S, Menegazzi JJ, Van Ottingham L, Olsufka M, Pennington S, Simonini J, Berg RA, Stiell I, Idris A, Bigham B, Morrison L; Resuscitation Outcomes Consortium (ROC) Investigators. Perishock pause: an independent predictor of survival from out-of-hospital shockable cardiac arrest. Circulation. Jul. 5, 2011;124(1):58-66. doi: 10.1161/CIRCULATIONAHA.110.010736. Epub Jun. 20, 2011. PMID: 21690495; PMCID: PMC3138806.
S. Cheskes et al., "The impact of peri-shock pause on survival from out-of-hospital shockable cardiac arrest during the Resuscitation Outcomes Consortium PRIMED trial," Resuscitation, vol. 85, No. 3, pp. 336-342, 2014 https://doi.org/10.1016/j.resuscitation.2013.10.014.
Gamboa, J. C. B. (2017). Deep learning for time-series analysis. arXiv preprint arXiv:1701.01887.
A. Krizhevsky, I. Sutskever, and G. E. Hinton, "ImageNet Classification with Deep Convolutional Neural Networks," Adv. Neural Inf. Process. Syst., pp. 1-9, 2012. Available online at: https://proceedings.neurips.cc/paper/2012/file/c399862d3b9d6b76c8436e924a68c45b-Paper.pdf.
G. Hinton et al., "Deep Neural Networks for Acoustic Modeling in Speech Recognition," IEEE Signal Process. Mag., No. November, pp. 82-97, 2012. Digital Object Identifier 10.1109/MSP.2012.2205597.
I. Sutskever, O. Vinyals, and Q. V Le, "Sequence to sequence learning with neural networks," Adv. Neural Inf. Process. Syst., pp. 3104-3112, 2014. arXiv:1409.3215.
R. Collobert, J. Weston, L. Bottou, M. Karlen, K. Kavukcuoglu, and P. Kuksa, "Natural Language Processing (Almost) from Scratch," J. Mach. Learn. Res., vol. 12, pp. 2493-2537, 2011.
LeCun, Y., Bengio, Y. & Hinton, G. Deep learning. Nature 521, 436-444 (2015). https://doi.org/10.1038/nature 14539.
Alipanahi B, Delong A, Weirauch MT, Frey BJ. Predicting the sequence specificities of DNA- and RNA-binding proteins by deep learning. Nat Biotechnol. Aug. 2015;33(8):831-8. doi: 10.1038/nbt.3300. Epub Jul. 27, 2015. PMID: 26213851.
Ma J, Sheridan RP, Liaw A, Dahl GE, Svetnik V. Deep neural nets as a method for quantitative structure-activity relationships. J Chem Inf Model. Feb. 23, 2015;55(2):263-74. doi: 10.1021/ci500747n. Epub Feb. 17, 2015. PMID: 25635324.
A. van den Oord et al., "WaveNet: A Generative Model for Raw Audio," pp. 1-15, 2016. arXiv:1609.03499v2.
Sepp Hochreiter, Jürgen Schmidhuber; Long Short-Term Memory. Neural Comput 1997; 9 (8): 1735-1780. doi: https://doi.org/10.1162/neco.1997.9.8.1735.
K. Greff, R. K. Srivastava, J. Koutnik, B. R. Steunebrink, and J. Schmidhuber, "LSTM: A Search Space Odyssey," IEEE Trans. Neural Networks Learn. Syst., vol. 28, No. 10, pp. 2222-2232, 2017. arXiv:1503.04069v2.
Bai, S., Kolter, J. Z., & Koltun, V. (2018). An empirical evaluation of generic convolutional and recurrent networks for sequence modeling. arXiv preprint arXiv:1803.01271.

(56) References Cited

OTHER PUBLICATIONS

Yaniv Y, Lyashkov AE, Lakatta EG. Impaired signaling intrinsic to sinoatrial node pacemaker cells affects heart rate variability during cardiac disease. J Clin Trials. Mar. 2014,4(1):152. doi: 10.4172/2167-0870.1000152. PMID: 26251764; PMCID: PMC4524547.

Lomb, N.R. Least-squares frequency analysis of unequally spaced data. Astrophys Space Sci 39, 447-462 (1976). https://doi.org/10.1007/BF00648343.

M. D. Costa, R. B. Davis, and A. L. Goldberger, "Heart rate fragmentation: A new approach to the analysis of cardiac interbeat interval dynamics," Front. Physiol., vol. 8, No. May, pp. 1-13, 2017. doi: 10.3389/fphys.2017.00255.

Chollet, F. & others, 2015. Keras. Available at: https://github.com/fchollet/keras.

S. D. Greenwald and S. D. Greenwald, "The Development and Analysis of a Ventricular Fibrillation Detector," Massachusetts Institute of Technology, 1986.

Simona Petrutiu, Alan V. Sahakian, Steven Swiryn, Abrupt changes in fibrillatory wave characteristics at the termination of paroxysmal atrial fibrillation in humans, EP Europace, vol. 9, Issue 7, Jul. 2007, pp. 466-470, https://doi.org/10.1093/europace/eum096.

Gliner V, Behar J, Yaniv Y. Novel Method to Efficiently Create an mHealth App: Implementation of a Real-Time Electrocardiogram R Peak Detector. JMIR Mhealth Uhealth. May 22, 2018;6(5):e118. doi: 10.2196/mhealth.8429. PMID: 29789276; PMCID: PMC5989064.

N. Srivastava, G. Hinton, A. Krizhevsky, I. Sutskever, and R. Salakhutdinov, "Dropout: A Simple Way to Prevent Neural Networks from Overfitting," J. Mach. Learn. Res., vol. 15, pp. 1929-1958, 2014.

Kingma, D. P., & Ba, J. (2014). Adam: A method for stochastic optimization. arXiv preprint arXiv:1412.6980.

M. Abadi et al., "TensorFlow: A System for Large-Scale Machine Learning TensorFlow: A system for large-scale machine learning," in 12th USENIX Symposium on Operating Systems Design and Implementation (OSDI '16), 2016.

N. Keidar, "jVec," 2018. [Online]. Available: https://github.com/redjest/jvec.

PCT International Search Report for International Application No. PCT/IL2019/050999, dated Dec. 19, 2019, 4pp.

PCT Written Opinion for International Application No. PCT/IL2019/050999, dated Dec. 31, 2019, 5pp.

\* cited by examiner

PREDICTING VENTRICULAR FIBRILLATION

CROSS REFERENCE TO RELATED APPLICATIONS

This application is a National Phase of PCT Patent Application No. PCT/IL2019/050999 having International filing date of Sep. 5, 2019, which claims the benefit of priority from U.S. Provisional Patent Application No. 62/727,611, filed on Sep. 6, 2018, entitled "PREDICTING VENTRICULAR FIBRILLATION," the contents of which are all incorporated by reference herein in their entirety.

FIELD OF THE INVENTION

The invention relates to methods for predicting ventricular fibrillation.

BACKGROUND OF THE INVENTION

Cardiovascular disease is the most prevalent cause of death in the developed world, responsible for 35% of all death cases in the US. It is estimated that ~50% of cardiac death cases are sudden, and that up to two-thirds of sudden cardiac death (SCD) cases occur as the first clinical manifestation of a major cardiac disorder. Current literature states that in 25%-35% of all cardiac arrest cases, the rhythm recorded in first contact with the patient is VF. In 50% of all cases in which asystole is measured, it is estimated that the vast majority were preceded by VF.

The immediate treatment of VF is cardiopulmonary resuscitation to preserve brain perfusion, followed by the administration of an electric shock (defibrillation) in order to restore sinus rhythm. Success rates of immediate resuscitation in primary cardiac arrest during acute myocardial infarction in a monitored setting exceed 90%. Survival rates are thought to decrease linearly by 10% for each minute passing between the onset of VF and beginning of resuscitation. The importance of immediate treatment is further emphasized by the fact that most of the patients that do survive after a 4 to 6 minute delay in treatment (25-30%), suffer extensive and irreversible brain damage.

The importance of immediate treatment has led to the implementation of community response systems and deployment of automatic external defibrillators. These steps have significantly improved the survival rate in out-of-hospital settings, but there is still room for improvement. For very high-risk patients who experience frequent bouts of VF, the treatment of choice is an implantable cardioverter defibrillator (ICD)—a device that continuously monitors the electrical activity of the heart and terminates VF events by delivering a burst of fast pacing or an electric shock if needed. ICD candidates comprise a negligible fraction of total SCDs in the general population.

Several research groups have attempted to develop algorithms that successfully predict VF. Li & Dong implemented a VF detection and prediction algorithm based on methods from complex network theory (X. Li and Z. Dong, "Detection and prediction of the onset of human ventricular fibrillation: An approach based on complex network theory," Phys. Rev. E-Stat. Nonlinear, Soft Matter Phys., vol. 84, no. 6, pp. 1-4, 2011). They applied a visibility graph method on 10-second ECG time series to identify the prevalence of different motifs and classified the interval as VF or normal sinus rhythm with sensitivity and specificity of 96.5% and 89.5%, respectively. VF onset was predicted based on the mean rate of change in the prevalence of the various motifs, with sensitivity of 85% and specificity of 88.8%, 5 to 290 seconds before onset.

Nearing & Verrier developed a robust algorithm for measuring T-wave alternans (the fluctuations in the amplitude of T-waves in ECG data), which have been shown to have a strong correlation with VF (B. D. Nearing and R. L. Verrier, "Modified moving average analysis of T-wave alternans to predict ventricular fibrillation with high accuracy," J. Appl. Physiol., vol. 92, no. 2, pp. 541-549, 2002). They developed an algorithm for analysis of variations in heart rate, noise, and other interferences. The algorithm (termed "modified moving average analysis of T-wave alternans") analyses ECG data in the time domain, and subsequently can be used in real time for the prediction of VF.

In both these cases, the authors used ECG readings as their source for predicting VF. However, it is unrealistic for the patients to wear a mobile ECG monitor continuously. Moreover, Nearing and Verrier make no mention of the exact time interval used for prediction, and how early it was prior to the onset of VF.

Other research groups used heart rate variability (HRV) parameters as their basis for prediction. Sarusi et al. investigated the predictive power of beat to beat variability (BVI) for VF in ischemic isolated mouse hearts (A. Sarusi et al., "Absolute beat-to-beat variability and instability parameters of ECG intervals: Biomarkers for predicting ischaemia-induced ventricular fibrillation," Br. J. Pharmacol., vol. 171, no. 7, pp. 1772-1782, 2014). They measured ECG signals of various length and found that absolute (not omitting abnormal sinus rhythm intervals) BVI parameters which quantify the variability of the repolarization had the best predictive power. However, these experiments were performed on isolated hearts and not on humans.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

The following embodiments and aspects thereof are described and illustrated in conjunction with systems, tools and methods which are meant to be exemplary and illustrative, not limiting in scope.

There is provided, in an embodiment, a method comprising: at a training stage, training a machine learning algorithm on a training set comprising: (i) Heart Rate Variability (HRV) parameters extracted from temporal beat activity samples, wherein at least some of said samples include a representation of a Ventricular Fibrillation (VF) event, and (ii) labels associated with one of: a first period of time immediately preceding a VF event in a temporal beat activity sample, a second period of time immediately preceding the first period of time in a temporal beat activity sample, and all other periods of time in a temporal beat activity sample; at an inference stage, receiving, as input, a target HRV parameters representing temporal beat activity in a subject; and applying said machine learning algorithm to said target HRV parameters, to predict an onset time of a VF event in said subject.

There is also provided, in an embodiment, a system comprising at least one hardware processor; and a non-transitory computer-readable storage medium having stored thereon program code, the program code executable by the at least one hardware processor to: at a training stage, training a machine learning algorithm on a training set comprising: (i) Heart Rate Variability (HRV) parameters extracted from temporal beat activity samples, wherein at least some of said samples include a representation of a Ventricular Fibrillation (VF) event, and (ii) labels associated with one of: a first period of time immediately preceding a VF event in a temporal beat activity sample, a second period of time immediately preceding the first period of time in a temporal beat activity sample, and all other periods of time in a temporal beat activity sample; at an inference stage, receiving, as input, a target HRV parameters representing temporal beat activity in a subject; and applying said machine learning algorithm to said target HRV parameters, to predict an onset time of a VF event in said subject.

There is further provided, in an embodiment, a computer program product comprising a non-transitory computer-readable storage medium having program code embodied therewith, the program code executable by at least one hardware processor to: at a training stage, training a machine learning algorithm on a training set comprising: (i) Heart Rate Variability (HRV) parameters extracted from temporal beat activity samples, wherein at least some of said samples include a representation of a Ventricular Fibrillation (VF) event, and (ii) labels associated with one of: a first period of time immediately preceding a VF event in a temporal beat activity sample, a second period of time immediately preceding the first period of time in a temporal beat activity sample, and all other periods of time in a temporal beat activity sample; at an inference stage, receiving, as input, a target HRV parameters representing temporal beat activity in a subject; and applying said machine learning algorithm to said target HRV parameters, to predict an onset time of a VF event in said subject.

In some embodiments, some of said samples do not include a representation of a VF event.

In some embodiments, said target HRV parameters are extracted from a signal representing beat activity, and wherein said signal is acquired from said subject in real time.

In some embodiments, the method further comprises segmenting, and the program instructions are further executable to segment, said target signal into a series of consecutive segments, wherein each of said segments comprises (i) a current beat, and (ii) a specified number of immediately preceding beats.

In some embodiments, said specified number is between 60 and 1000.

In some embodiments, said extracting comprises continuously extracting said target HRV parameters from each of said segments in said series of consecutive segments, and wherein said applying comprises applying said machine learning algorithm to each of said extracted c HRV parameters.

In some embodiments, said training set is generated by: (i) dividing each of said samples into a plurality of sample segments, based, at least in part, on a specified minimum number of said beats in each of said sample segments; (ii) randomly selecting one or more subsets of said sample segments from said plurality of sample segments; and (iii) combining one or more of said subsets into said training set.

In some embodiments, said specified minimum number is determined, at least in part, based on a size of a desired receptive field of said machine learning model.

In some embodiments, said segmenting is based, at least in part, on detecting beat intervals in said signal.

In some embodiments, said HRV parameters and target HV parameters are determined, at least in part, based on an HRV feature vector extracted from said signal.

In some embodiments, said signal is at least one of an action potential signal, an electrogram signal, an electrocardiograph (ECG) signal, and a photoplethysmogram (PPG) signal.

In some embodiments, said HRV parameters and said target HRV parameters include at least one of: Average NN interval duration (AVNN); standard deviation of NN interval duration (SDNN); a square root of the mean of the sum of the squares of differences between adjacent NN intervals (RMSDD); percent of NN interval differences greater than xx milliseconds (pNNxx); coefficient of variation (CV); variance of the Modified Shannon Entropy across consecutive beat intervals (yyVar); very low frequency (VLF) band power; low frequency (LF) band power; high frequency (HF) band power; VLF, LF, and HF power combined; ratio between VLF power and the power of all VLF, LF, and HF bands combined; ratio between LF power and the power of VLF, LF, and HF bands combined; ratio between HF power and the power of all VLF, LF, and HF bands combined; ratio between LF power and HF power; slope of the log-log frequency plot in the VLF band; percentage of inflection points (PIP); inverse average length of the acceleration/deceleration segments (IALS); percentage of short segments (PSS); and a percentage of NN intervals in alternation segments (PAS).

In some embodiments said predicting further comprises issuing a notification with respect to said onset time of said VF event, and wherein said notifications is issued within a specified time of said predicted onset time of said VF event.

In some embodiments, said extracting further comprises filtering said signal to remove beats associated with non-normal sinus node polarizations.

In some embodiments, said filtering is based on one or more of: range-based filtering, moving average filtering, and quotient filtering.

In some embodiments, said machine learning model comprises a convolutional neural network (CNN).

In some embodiments, said CNN is a temporal convolutional network (TCN).

In some embodiments, said samples are labelled with said labels.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
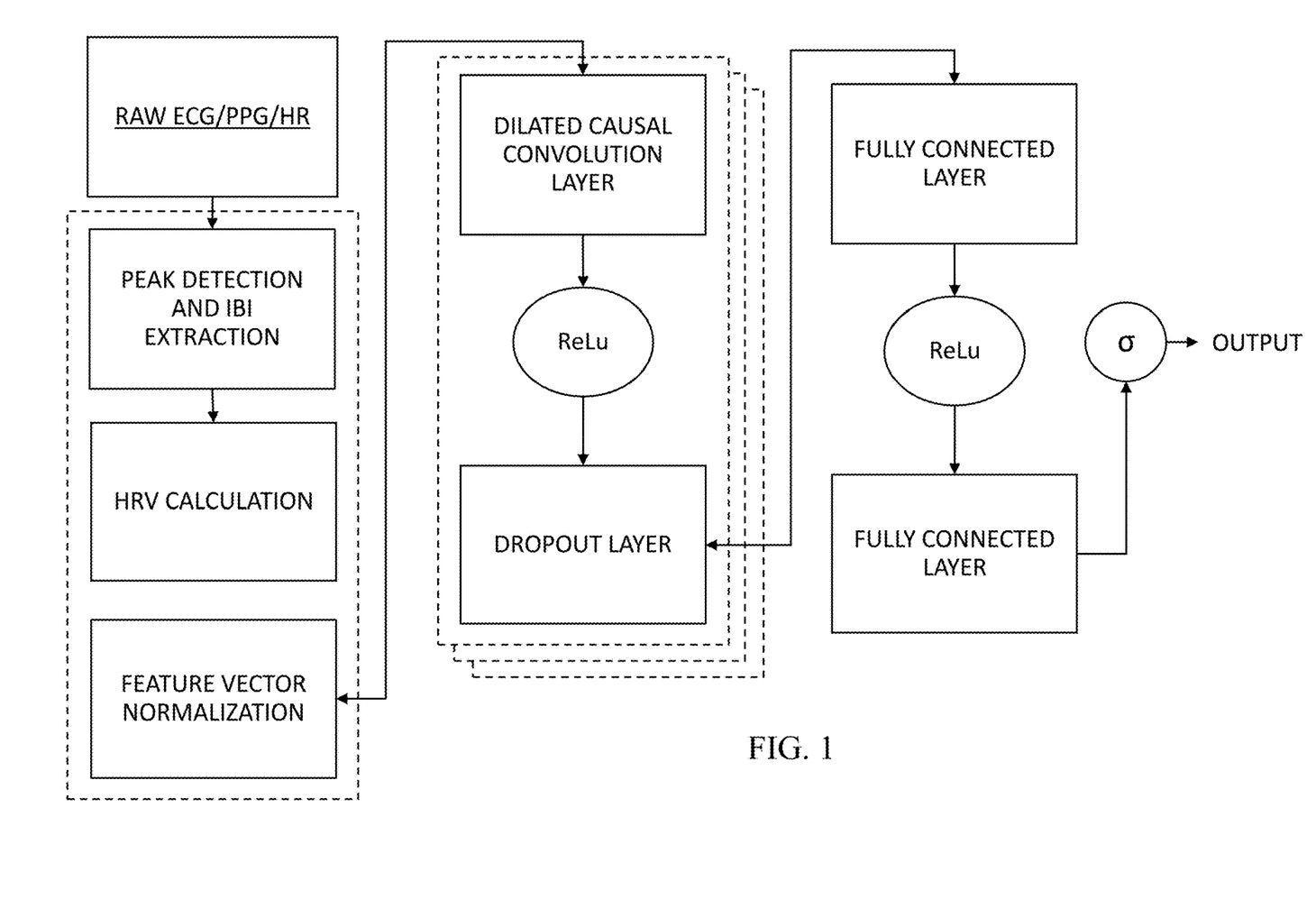
FIG. 1 illustrates an exemplary system architecture, according to an embodiment.
Figure 2:
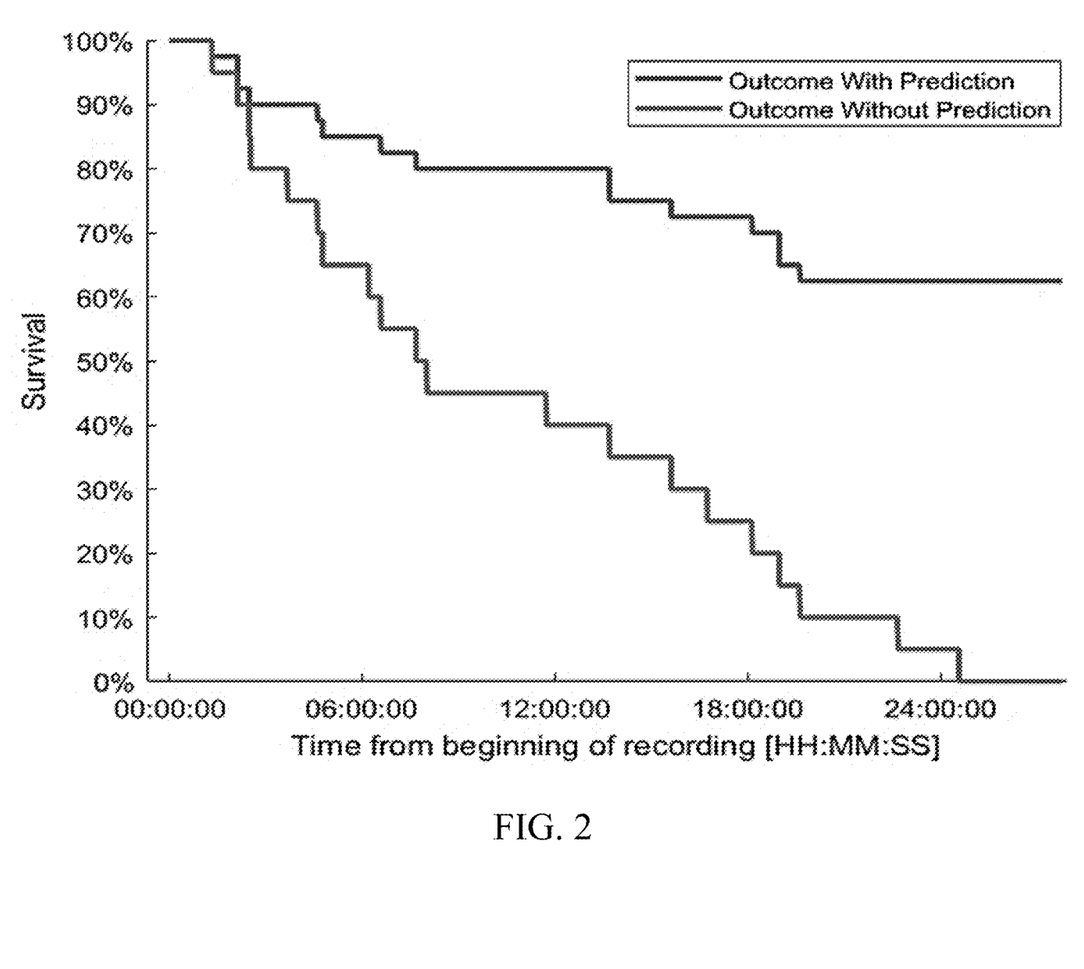
FIG. 2 illustrates the results of the prediction model on the entire study cohort presented as a Kaplan-Meyer curve, in which the base assumption was that a successfully predicted event was prevented and the patient survived.
Figure 3:
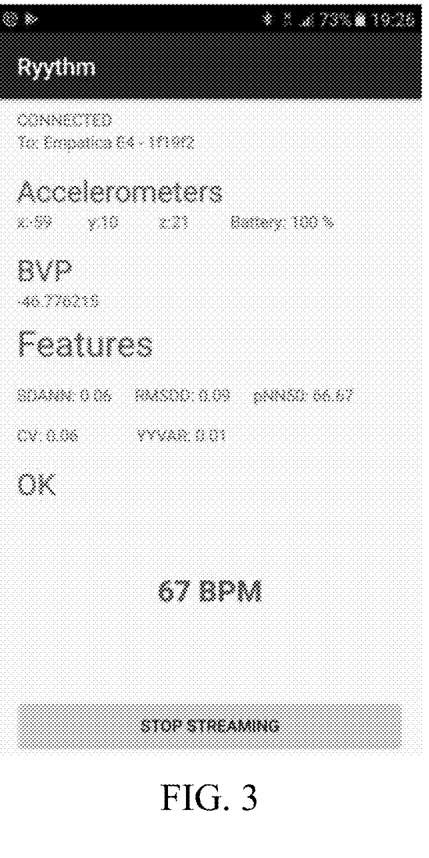
FIG. 3 illustrates the interface of an application running the computer program product of the invention, according to an embodiment.

Disclosed herein are a system, method, and computer program product for monitoring for imminent ventricular fibrillation (VF) events. These may be embodied, for example, in a portable computing device, optionally a wearable one (e.g. a computerized wristband, computerized watch, etc.), which continually monitors a subject at risk for a VF event or a computer program product that calculates the risk of VF from physiological signals that were measured by such device and transmitted to the computer.

The operation of the heart can be thought of as a dynamic process, with the difference in electric potential between electrodes connected to the body or the infrared light absorbance of the finger as the signal and the electrocardiogram (ECG) or photoplethysmogram (PPG) as a time series. Another signal that may be derived from the heart's activity is heart rate and the corresponding time series is the lengths of time intervals between consecutive beats. the annotation x(t) will be used for a continuous time signal, and the annotation x[n] for the nth sample in the time series.

In some embodiments, machine learning algorithms may be used for time series analysis. Classic models such as fully connected neural networks are hard to use because of the varying length of inputs and the high computational cost. Thus, two specialized model architectures were developed for data with serial nature as the time series: recurrent neural networks and temporal convolutional networks.

Recurrent neural networks (RNN) are artificial neural networks that process serial data one step at a time. Convolutional Neural Networks (CNN) are a class of artificial neural networks that have been applied to sequences for decades, and Temporal Convolutional Networks (TCN) are a subtype of CNN optimized for dealing with data sequences in real time. The networks receptive field in the present case is the length of history that the network takes into account at any given moment. In order to enhance the receptive field without significantly deepening the network one can employ dilated convolution. Formally, for an input sequence x[n] and a kernel h of length k, the dilated convolution operation of the sequence is defined as:

$$y[n] = x * h_d = \sum_{i=0}^{k-1} x[i]h[n - d \cdot i] \quad (1)$$

where d is the dilation factor. The receptive field can be increased in two ways: choosing a larger kernel size k and increasing the dilation factor d. The receptive field size can be calculated as follows:

$$RF = (k-1)(d^{N+1} - 1) \quad (2)$$

There are many additional advantages of using TCNs for sequence modeling over traditional CNNs or RNNs [17]: TCN models can be run in parallel using minimal computational power, they avoid the vanishing gradient problem, they have low memory requirements for training and they can receive inputs of varying length.

Heart Rate Variability

Normal heart rate is relatively, but not completely, regular. Variations in heart rate, even between consecutive beats, are thought to store important information regarding the heart's health. Thus, many methods have been devised to extract significant features from the heart rate variability (HRV) time series. These methods can be divided into three main categories: time domain, frequency domain and nonlinear features.

Heart Rate Variability—Time Domain

Time-series analysis is a relatively simple means of evaluating HRV over time. The time domain features there were used are the following:

AVNN—the mean of all beat intervals in a time window of length N beat intervals:

$$AVNN = \frac{\sum_{i=1}^{N} x_i}{N} = \bar{x} \quad (3)$$

SDNN—The standard deviation of all beat intervals in a time window:

$$SDNN = \sqrt{\frac{\sum_{i=1}^{N} (x_i - \bar{x})^2}{N - 1}} \quad (4)$$

RMSDD—The square root of the mean of squares of successive beat intervals:

$$RMSDD = \sqrt{\frac{\sum_{i=1}^{N-1} (x_{i-1} - x_i)^2}{N - 1}} \quad (5)$$

pNN50—The percentage of beat intervals with a difference of 50 milliseconds or more from their preceding interval:

$$pNN50 = \frac{\sum_{i=1}^{N} \mathbb{I}\{(x_{i+1} - x_i) > 50 \text{ ms}\}}{N - 1} \cdot 100\% \quad (6)$$

where $\mathbb{I}$ is the Indicator Function and beat intervals are measured in milliseconds.

CV—Coefficient of variation of all beat intervals in a time window. It is the quotient of AVNN and SDNN:

$$CV = \frac{AVNN}{SDNN} \quad (7)$$

yyVAR—The variance of the Modified Shannon Entropy across 3 consecutive beat intervals:
Firstly, let the Modified Shannon Entropy be defined as the difference between the absolute differences between 2 consecutive pairs in a 3-beat window:

$$\hat{S}_i = |x_{i-2} - x_{i-1}| - |x_{i-1} - x_i| \quad (8)$$

The average entropy is as follows:

$$\bar{S} = \frac{\sum_{i=3}^{N} \hat{S}_i}{N - 2} \quad (9)$$

Thus, the variance can be defined as:

$$yyVAR = \frac{\sum_{i=3}^{N} (\hat{S}_i - \bar{S})^2}{N - 3} \quad (10)$$

Heart Rate Variability—Frequency Domain

In order to quantify cyclic fluctuations of beat intervals in a specific time window, their power spectrum was calculated via the Lomb Periodogram, and various features were extracted from it. Three specific frequency bands that have been found to have physiological relevance were analyzed:

| Frequency Band | Range |
| --- | --- |
| Very low frequency (VLF) | 0.003-0.04 Hz |
| Low Frequency (LF) | 0.04-0.15 Hz |
| High frequency (HF) | 0.15-0.4 Hz |

Frequency Domain Features are as follows:

| Feature Name | Description |
| --- | --- |
| VLF Power | Total power in the VLF band |
| LF Power | Total power in the LF band |
| HF Power | Total power in the HF band |
| Total Power | Total power in all 3 bands combined |
| VLF Norm | The ration between VLF power and the power of all 3 bands combined |
| LF Norm | The ration between LF power and the power of all 3 bands combined |
| HF Norm | The ration between HF power and the power of all 3 bands combined |
| LF to HF | The ration between LF power and HF power |
| Beta | Slope of the log-log frequency plot in the VLF band, calculated using the LMS technique |

Nonlinear Methods

Due to the chaotic nature of the heart, nonlinear methods must be employed to characterize its complex dynamics. One way to characterize such dynamics is through heart rate fragmentation [20]. Firstly, let the difference between consecutive beat intervals be defined as:

$$\Delta x_i = x_i - x_{i-1}$$

The features that were used are as follows:
- PIP—Percentage of inflection points: $x_i$ is an inflection point if $\Delta x_i \Delta x_{i+1} \leq 0$, that is to say, in $x_i$ there is an inversion in the sign of heart rate acceleration.
- IALS—The inverse of the average length of segments between inflection points (segments of acceleration/deceleration).
- PSS—Percentage of beat intervals that are in short segments between inflection points (3 or less).
- PAS—Percentage of beat intervals that are in alternation segments of at least 4 intervals. An alternation segment is a segment of 4 consecutive beat intervals for which all of them are inflection points.

Data

Due to the abrupt and lethal nature of VF, ECG recordings containing events are few and far between. Furthermore, the onset itself of VF can be termed a "rare event", as in, it happens only once per recording (if at all) and is represented by a single data point out of thousands or millions per recording. These factors were challenging to overcome, both in data acquisition and in the ability to deduce from a handful of samples to the general population.

The present system was trained and tested using ECG recordings from PhysioBank (see A. L. Goldberger et al., "PhysioBank, PhysioToolkit, and PhysioNet: Components of a New Research Resource for Complex Physiologic Signals," *Circulation,* vol. 101, no. 23, pp. e215-e220, 2000). The specific databases used were the following:

Sudden Cardiac Death Holter Database—23 complete Holter recordings of varying duration (7-24 hours). They include 13 men, ages 17-80, 8 women, ages 30-89 and 2 gender unknown. 3 recordings were excluded—2 were artificially paced and the $3^{rd}$ didn't contain a VF event.

The MIT-BIH Normal Sinus Rhythm Database—18 long-term ECG recordings of subjects that were found to have had no significant arrhythmias. They include 5 men, aged 26 to 45, and 13 women, aged 20 to 50. One recording was excluded for being of poor quality.

The Long-Term Atrial Fibrillation Database—84 long-term ECG recordings of subjects with paroxysmal or sustained atrial fibrillation (AF), typically 24-25 hours long. Only 43 recordings were used, because many were excluded for being of poor quality.

System Overview

In some embodiments, the present invention provides for training a machine learning model (e.g., a classification-type model or a regression-type model) on a training set comprising a plurality of temporal beat activity samples, wherein some of the beat activity samples are associated with a VF event, and some are not (and were either recorded in healthy individuals, in VF-prone individuals who did not have a VF event at the time of recording, or in individuals suffering from other, non-VF, cardiac conditions).

For samples that are associated with a VF event, (a) a certain period of time immediately preceding the event is labeled with a first label (referred to herein as "alarm desirable"), that indicates an alarm will be desirable for similar HRV patterns at the inference stage, (b) another period of time, immediately preceding the one labeled with the first label, is labeled with a second label (referred to herein as "irrelevant" or the like), which prevents the model from giving this period a penalty (and thereby incorrectly biasing the decision of whether to alarm or not when such patterns occur), and (c) the remainder of the sample is labeled with a third label, (referred to herein as "alarm undesirable") that indicates an alarm is not desirable for similar HRV patterns at the inference stage. These labels are merely textual descriptions of their nature, and it is explicitly intended that any label may be used during training, as long as there is a differentiation between the various categories.

For samples that are not associated with a VF event, such as samples from healthy patients and from patients with non-VF heart conditions, the label is "alarm undesirable" for the entire duration of the beat activity samples.

In some embodiments, the model may be trained multiple times, every time with a different length of time labeled with the first label (alarm desirable). For example, that length of time may be set to a different value in the range of 1-60 minutes (including any integer or decimal value in that range) for each discrete training. Each possibility represents a separate embodiment of the invention. Then, the accuracy (e.g., specificity and/or sensitivity) of each trained model may be tested, and the best-performing model chosen as the one to be used at the inference stage.

Notably, even if a time length X is used for "alarm desirable" in the training, VF events may be occasionally alerted at the inference stage even beyond X minutes/seconds before a VF event. Namely, time length X is chosen during training because it is a period very close to the VF event and therefore highly likely to include HRV patterns that are unique to the onset of the event. At inference time, it is likely that the same HRV pattern will occur even earlier than in the training samples—and alerting as to such earlier occurrence is certainly desirable.

In some embodiments, the trained model is used for inference for multiple patients, without change. In other embodiments, training is performed de-novo for each patient based on recordings from that particular patient. For example, a patent attached to a monitoring device may first undergo a training period in which no alerting is performed, but rather a patient-specific model is trained based on the beat activity of the patient and labels that are manually added to that activity. After training is done, the model will begin issuing alerts whenever an HRV pattern associated with an onset of VF is detected. In yet other embodiments, a combination of patient-specific training, and training that was preformed for other patients, is used. The patient-specific training will improve the model and allow it to detect pattern intricacies not necessarily exhibited in samples obtained for other patients.

In some embodiments, the beat activity samples are preprocessed, to extract a plurality of HRV parameters associated with each of the beat activity samples.

In some embodiments, in an inference stage, a machine learning model is applied to an input signal representing temporal beat activity in a subject, to predict an onset time of a VF event in said subject.

In some embodiments, the input signal is preprocessed in a process similar to the one applied to the training set, to automatically extracting runtime HRV parameters from the signal.

In some embodiments, the input signal is a continuous signal received in real time. In some embodiments, the input signal is segmented into a continuous series of segments, wherein each of said segments comprises (i) a current beat, plus (ii) a specified number of immediately preceding beats, e.g., 120 beats, for a total of 121 beats in each segment.

In some embodiments, the specified number of beats is between 50-2000, 50-1500, 50-1000, 50-800, 50-600, 50-400, 50-200, 60-2000, 60-1500, 60-1000, 60-800, 60-600, 60-400, 60-200, 70-2000, 70-1500, 70-1000, 70-800, 70-600, 70-400, 70-200, 80-2000, 80-1500, 80-1000, 80-800, 80-600, 80-400, 80-200, 90-2000, 90-1500, 90-1000, 90-800, 90-600, 90-400, 90-200, 100-2000, 100-1500, 100-1000, 100-800, 100-600, 100-400, or 100-200 beats. Each possibility represents a separate embodiment of the invention.

In some embodiments, the machine learning model is configured for continuously predicting an onset time of a VF event in each of the segments. In some embodiments, a system of the present invention is configured for issuing a suitable notification in connection with a predicted onset time of a VF event.

In some embodiments, the training stage and/or the inference stage may be performed by a computerized wearable device such as a computerized wristband, a computerized watch, a computerized adhesive patch, a computerized waist band or chest band, or the like. The computerized wearable device may include a heartbeat sensor, such as a PPG sensor or an ECG sensor, configured to sense temporal beat activity in the subject wearing the device. The computerized wearable device may further include a processor and instructions stored on a non-transient memory, which instructions perform the steps of the training and/or inference stages.

In some embodiments, the training stage and/or the inference stage may be performed, at least in part, by a non-wearable monitoring device which includes a heartbeat sensor, such as a PPG sensor or an ECG sensor, configured to sense temporal beat activity in a subject attached to the sensor, and optionally a processor and instructions stored on a non-transient memory, which instructions perform the steps of the training and/or inference stages. Alternatively, the processing may be performed externally to the monitoring device.

Preprocessing of Beat Activity Data

In some embodiments, in a preprocessing stage applicable both to runtime beat activity data and training beat activity data, physiological input signals may be preprocessed to obtain a plurality of HRV-related measurements. In some embodiments, IBIs may be obtained via R peak detection in ECG recordings using a state-of-the-art peak detector. Peak detection yields a vector of all beat times (BT) from the beginning of the recording up to the current time point for which will be used the notation:

$$\vec{BT}(t) = \begin{pmatrix} BT_1 \\ BT_2 \\ \vdots \\ BT_n \end{pmatrix} \Big| BT_k \leq t \,\forall\, k = 1, 2, \ldots, n \quad (11)$$

For every new beat detected, let us define the vector of the last N IBIs:

$$\vec{RP}[n] = \begin{pmatrix} BT_{n-N+1} - BT_{n-N} \\ \vdots \\ BT_{n-1} - BT_{n-2} \\ BT_n - BT_{n-1} \end{pmatrix} \quad (12)$$

This vector was named the "recent past" (RP) vector. Now a feature space representation of the RP vector using M HRV indices may be defined:

$$\vec{\phi}[n] = \begin{pmatrix} \phi_1(\vec{RP}[n]) \\ \phi_2(\vec{RP}[n]) \\ \vdots \\ \phi_M(\vec{RP}[n]) \end{pmatrix} \quad (13)$$

Used N=121, M=19 and the HRV indices listed above (Methods, Subsection C—Heart Rate Variability) were used. The feature vector was normalized using Z-score normalization:

$$\vec{\phi}'[n] = \frac{\vec{\phi}[n] - \vec{\mu}}{\vec{\sigma}} \quad (14)$$

Where, $\vec{\mu}$ is a vector of the means of the HRV indices and $\vec{\sigma}$ is their standard deviations. There is now can be defined the history matrix as a matrix containing all the normalized feature vectors until a certain time point, t, as a row of column vectors:

$$\Phi(t) = (\vec{\phi}[N], \vec{\phi}[N+1], \ldots, \vec{\phi}[n]) \quad (15)$$

Alarm Desirability Function

In order to model the prediction of a rare event as a supervised learning problem and maintain causality, an advantageous approach was used referred to as the Alarm Desirability Function (ADF). Let us consider a function:

$$\Psi: \mathbb{R}^{n \times M} \to [0,1] \quad (16)$$

It is assumed that at time $t_{on}$ there is an onset of a VF event in the recording. For recordings without events $t_{on}$ may be thought of as infinity.

The desirable time for alarm is defined as $\Delta t_{al}$ and a time interval before it, in which an alarm is desirable, but not alarming is not a mistake, as the "Irrelevant" zone of length $\Delta t_{dc}$.

The ADF is defined as:

$$\Psi(t) = \begin{cases} 0 & t < t_{on} - \Delta t_{al} - \Delta t_{dc} \\ 1 & t_{on} - \Delta t_{al} < t < t_{on} \\ \text{arbitrary} & \text{else} \end{cases} \quad (17)$$

The ADF is used as the "ground truth" for the prediction model. The considerations for defining the ADF will be elaborated upon in the discussion section of this paper.

A. Model

The prediction model itself may be thought of as an estimator of the ADF based on real time measurements of IBIs:

$$\hat{\Psi}(t) = \hat{\Psi}(\overrightarrow{BT}(t)) \quad (18)$$

Due to the use of IBIS rather than the raw ECG signal as an input to the model, half an hour history is represented by ~2000 time-steps, which means that a considerably small TCN may be sufficient to have an adequate temporal receptive field. A model with 7 causal diluted convolution layers and a kernel length of 9 was used, which according to (eq. 2) gives a T=2295 time-step receptive field. The number of filters was 32 for each convolution layer, the activation function used was ReLu and a dropout layer was added after each convolution layer. The output of the convolutional block was adapted to be a 1-dimensional vector in range [0,1] using 2 fully connected layers with a ReLu activation function in the first and a sigmoid activation function in the second.

Generating the Training Set

Due to the small number of recordings that contain VF events, there had to be found a way to present different versions of the same event to the model, in order to maximize the learning potential per sample. The following training paradigm, termed *Spotlight Training*, was found to provide favorable results.

Consider a set of S samples:

$$X = \{\Phi_1, \Phi_2, \ldots, \Phi_S\} \quad (19)$$

with their corresponding ADFs:

$$Y = \{\Psi(\Phi_1), \Psi(\Phi_2), \ldots, \Psi(\Phi_S)\} \quad (20)$$

Note that $\Phi_k$ and $\Psi(\Phi_k)$ are time series of the same length. So, it can take a corresponding portion of the two series and use it as a new sample. A length for the split samples must now be selected, which is long enough for the entire receptive field, before the time of the alarm:

$$L > T + HR \cdot \frac{\Delta t_{al} + \Delta t_{dc}}{60} \quad (21)$$

where HR is the mean heart rate in BPM.

L=8192 was selected, which satisfies the restrictions in (21) and is still shorter than the shortest recording.

Now for each recording, there is provided a set of all possible divisions into k recording of length $l_k$:

$$x_k(i) = (\overrightarrow{\phi}[N+i], \overrightarrow{\phi}[N+i+1], \ldots, \overrightarrow{\phi}[N+i+L])$$
$$i = 0, 1, \ldots, l_k - N - L; \; k = 1, 2, \ldots, S \quad (22)$$

Next, a subset of these is randomly selected as the samples "under the spotlight" for the current epoch. By adjusting the probability for the selection of each sample, one may control the size of the training set, to ensure it fits into memory.

The training process is performed by minimalizing a modified version of binary cross entropy loss:

$$l(y, \hat{y}) = -1/2(\text{sign}(y)+1) \cdot (\alpha y \cdot \log(\hat{y}) + (1-y) \cdot \log(1-\hat{y}))$$
$$\alpha \in \mathbb{R}^+ \quad (23)$$

The supervision function is selected to be the ADF, with the value −1 in the "Irrelevant" regions. Thus, the first part of the argument ensures that the loss is zero in the "Irrelevant" regions, regardless of the output.

The constant $\alpha$ may be used to weigh the loss according to the prevalence of the events and correct the fact that the first part is doubled when y=1. However, there was not observed a great influence of the values of $\alpha$ on validation results, so for simplicity $\alpha=1$ was selected. For better generalization, added $L_2$ regularization was also added:

$$\tilde{l}(y, \hat{y}) = l(y, \hat{y}) + \lambda \|W\|^2 \quad (24)$$

The weight adjustment was done using the ADAM optimization algorithm.

Testing

The model was implemented using the Python wrapper library Keras with a TensorFlow backend. Due to the present dataset being relatively small, Leave-One-Out testing was used. Training was done on two GPUs: an NVIDIA® Tesla® K80 and an NVIDIA® Tesla® K20. It took about 120 hours total, mostly due to the Leave-One-Out testing. A single experiment took about 40 minutes.

Implementation

After training and testing, the computer program product of the invention was implemented as an Android application running locally on a mobile phone, using IBIs measured by an Empatica® E4 wristband, and streamed in real time to the phone using Bluetooth®. The app was tested on two devices: Samsung® Galaxy® S6 and S7. For efficient implementation of the prediction model and the preprocessing procedure, a streamlined open source vector operation JAVA library was built and termed jVec. Note that a single step of the TCN can be calculated on constant time complexity.

Results & Discussion

VF Prediction

Prediction results on the Leave-One-Out testing were calculated as follows: records containing a VF event for which the system alarmed at least 4 minutes in advance were counted as true positive (TP), records with an event for which there was no alarm at an appropriate time were considered as false negative (FN), records without an event for which there was an alarm were counted as false positive (FP) and as true negative (TN) if there was no alarm during the record. The experiment was run twice and will report the average results of both runs, due to the stochastic nature of the training of the model. As noted above:

$$\text{Specificity} = \frac{TN}{TN + FP} \quad (25)$$

$$\text{Sensitivity} = \frac{TP}{TP+FN} \quad (26)$$

A specificity of 100% and sensitivity of 62.5% were achieved. The high specificity is an encouraging result, all alarms were true alarms, which may suggest that when the present system does alarm, the alarm should be taken seriously. The moderate sensitivity is an expectable result because one of the prevalent mechanisms leading to VF is ischemia of the cardiac muscle. Such ischemia is usually caused by occlusion of a coronary artery. If, for example, the occlusion is caused by an embolus, it might be immediate, without any preceding process in the heart for a prediction algorithm to detect. The system did not trigger a single alarm for any of the healthy patients or the patients with heart arrythmias other than VF.

Model Architecture

Although even simple classification models, such as support vector machines (SVM), linear regression, decision trees, and simple feedforward neural networks, gave good (up to 98.5%) precision in classification of $\vec{\phi}[n]$ vectors to "preceding an event" and "not preceding an event", more detailed inspection showed that they can't be used as prediction systems. VF events are rare events, even on susceptible patients. Therefore, models with high classification precision were simple models that always classified to "not preceding an event". Even overfitting on a small dataset using actual clinical prediction performance measures gave poor results with such models. These results made us suspect that a longer history of HRV indices was needed.

The natural choice for a model with a longer memory was an LSTM, an architecture widely used for time series analysis. LSTM models were able to overfit a small dataset when model and training parameters were carefully chosen. However, the length of the IBI time series which was in the order of magnitude of $10^5$ made for very long training times, even when truncated backpropagation was used. When challenging the effective memory of the model was attempted with long (>150 timesteps) "Irrelevant" regions, LSTM models didn't manage even to overfit. The very long training times and the considerably short effective memory made the LSTM models irrelevant to the present problem.

Next the TCN models are tested. First, some overfitting experiments on single records was performed, which were an immediate success: training was ~2 orders of magnitude faster and the effective memory had no effective limits. The effective memory of a TCN is linear in the kernel length and exponential in the number of layers, so it is tempting to use deep architectures, and for some problems they are indeed necessary (like in raw audio generation, as was done in WaveNet). A model was aimed for that would fit in a mobile device, so WaveNet like architectures were irrelevant. Because IBIs were selected instead of a raw ECG signal, the "sampling rate" was approximately 1 Hz (if it is assumed that the heart rate to be 60 BPM), so an effective memory of 2000 timesteps corresponds to a ~30 minutes of the recording. Thus, only 7 diluted convolution layers could be used, with a kernel length of 9 and have a decent effective memory. Deeper models started to show vanishing gradient problems and require more sophisticated model architectures.

ADF Selection and Training

The ADF selection was dictated by practical and clinical considerations. As one may expect, longer $\Delta t_{al}$ decreased the tendency of the model to converge to zero (never sound an alarm) in the overfitting experiments. Longer $\Delta t_{dc}$ improved rate of convergence.

Because VF is a rare event, there is an inherent class imbalance in the data. Using the data as is, usually gave a convergence to zero, so two techniques were tried to balance the data: cost balancing and sample duplication. Cost balancing is done by giving different costs for the different classes. In the present cost function (eq. 23) it can be done by altering the $\alpha$ parameter. Sample duplication is simply overrepresentation of the rare class in the training set by duplicating the samples containing VF events. From the overfit experiments, the superiority of sample duplication to weighted cost in the prevention of convergence to zero was clear.

Mobile Device Implementation

The experimental application implementing the model on a mobile phone ran for full days without visibly affecting battery life or consuming more than 20 MB of RAM on the device.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++, Python or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration\ but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. A method of training a machine learning model to predict an onset of a Ventricular Fibrillation (VF) event, on a training set, the method comprising:
   (i) extracting Heart Rate Variability (HRV) parameters from temporal beat activity signal samples, wherein at least some of said samples include a representation of a VF event, and
   (ii) labelling the signal samples with labels associated with one of: a first period of time immediately preceding a VF event in a temporal beat activity sample, a second period of time immediately preceding the first period of time in a temporal beat activity sample, and all other periods of time in a temporal beat activity sample, wherein said training set is generated by:
   (i) segmenting each of said samples into a plurality of sample segments, based, at least in part, on a specified minimum number of said beats in each of said sample segments;
   (ii) randomly selecting one or more subsets of said sample segments from said plurality of sample segments; and
   (iii) combining one or more of said subsets into said training set.

2. The method of claim 1, wherein some of said samples do not include a representation of a VF event.

3. The method of claim 1, wherein said specified minimum number is determined, at least in part, based on a size of a desired receptive field of said machine learning model.

4. The method of claim 3, wherein said segmenting is based, at least in part, on detecting beat intervals in said signal samples.

5. The method of claim 1, wherein said HRV parameters are determined, at least in part, based on an HRV feature vector extracted from said signal samples.

6. The method of claim 1, wherein said signal is at least one of an action potential signal, an electrogram signal, an electrocardiograph (ECG) signal, and a photoplethysmogram (PPG) signal.

7. The method of claim 1, wherein said HRV parameters include at least one of: Average NN interval duration (AVNN); standard deviation of NN interval duration (SDNN); a square root of the mean of the sum of the squares of differences between adjacent NN intervals (RMSDD); percent of NN interval differences greater than xx milliseconds (pNNxx); coefficient of variation (CV); variance of the Modified Shannon Entropy across consecutive beat intervals (yyVar); very low frequency (VLF) band power; low frequency (LF) band power; high frequency (HF) band power; VLF, LF, and HF power combined; ratio between VLF power and the power of all VLF, LF, and HF bands combined; ratio between LF power and the power of VLF, LF, and HF bands combined; ratio between HF power and the power of all VLF, LF, and HF bands combined; ratio between LF power and HF power; slope of the log-log frequency plot in the VLF band; percentage of inflection points (PIP); inverse average length of the acceleration/deceleration segments (IALS); percentage of short segments (PSS); and a percentage of NN intervals in alternation segments (PAS).

8. The method of claim 1, wherein said extracting further comprises filtering said signal samples to remove beats associated with non-normal sinus node polarizations.

9. The method of claim 8, wherein said filtering is based on one or more of: range-based filtering, moving average filtering, and quotient filtering.

10. The method of claim 1, wherein said machine learning model comprises a convolutional neural network (CNN).

11. The method of claim 10, wherein said CNN is a temporal convolutional network (TCN).

12. A method of predicting an onset time of a VF event, the method comprising:
receiving, as input, target Heart Rate Variability (HRV) parameters representing temporal beat activity in a subject; and
applying a trained machine learning model to said target HRV parameters, to predict the onset time of a VF event in said subject,
wherein the machine learning model is a convolutional neural network (CNN) trained to predict an onset of a Ventricular Fibrillation (VF) event, on a training set comprising:
(i) Heart Rate Variability (HRV) parameters extracted from temporal beat activity signal samples, wherein at least some of said samples include a representation of a VF event, and
(ii) labels associated with one of: a first period of time immediately preceding a VF event in a temporal beat activity sample, a second period of time immediately preceding the first period of time in a temporal beat activity sample, and all other periods of time in a temporal beat activity sample,
wherein said training set is generated by:
(i) segmenting each of said samples into a plurality of sample segments, based, at least in part, on a specified minimum number of said beats in each of said sample segments;
(ii) randomly selecting one or more subsets of said sample segments from said plurality of sample segments; and
(iii) combining one or more of said subsets into said training set.

13. The method of claim 12, wherein said target HRV parameters are extracted from a signal representing beat activity, and wherein said signal is acquired from said subject in real time.

14. The method of claim 12, further comprising segmenting said target signal into a series of consecutive segments, wherein each of said segments comprises (i) a current beat, and (ii) a specified number of immediately preceding beats.

15. The method of claim 14, wherein said specified number is between 60 and 1000.

16. The method of claim 12, wherein said extracting comprises continuously extracting said target HRV parameters from each of said segments in said series of consecutive segments, and wherein said applying comprises applying said machine learning algorithm to each of said extracted c HRV parameters.

17. The method of claim 12, wherein said predicting further comprises issuing a notification with respect to said onset time of said VF event, and wherein said notifications is issued within a specified time of said predicted onset time of said VF event.

18. The method of claim 12, wherein said HRV parameters are determined, at least in part, based on an HRV feature vector extracted from said signal samples.

19. The method of claim 12, wherein said HRV parameters include at least one of: Average NN interval duration (AVNN); standard deviation of NN interval duration (SDNN); a square root of the mean of the sum of the squares of differences between adjacent NN intervals (RMSDD); percent of NN interval differences greater than xx milliseconds (pNNxx); coefficient of variation (CV); variance of the Modified Shannon Entropy across consecutive beat intervals (yyVar); very low frequency (VLF) band power; low frequency (LF) band power; high frequency (HF) band power; VLF, LF, and HF power combined; ratio between VLF power and the power of all VLF, LF, and HF bands combined; ratio between LF power and the power of VLF, LF, and HF bands combined; ratio between HF power and the power of all VLF, LF, and HF bands combined; ratio between LF power and HF power; slope of the log-log frequency plot in the VLF band; percentage of inflection points (PIP); inverse average length of the acceleration/deceleration segments (IALS); percentage of short segments (PSS); and a percentage of NN intervals in alternation segments (PAS).

* * * * *